United States Patent
Kulkarni et al.

(10) Patent No.: US 10,845,324 B2
(45) Date of Patent: Nov. 24, 2020

(54) TWO-DIMENSIONAL MATERIAL BASED ION EXCHANGE MEMBRANE SENSORS

(71) Applicant: THE REGENTS OF THE UNIVERSITY OF MICHIGAN, Ann Arbor, MI (US)

(72) Inventors: Girish Kulkarni, Ann Arbor, MI (US); Xudong Fan, Saline, MI (US); Zhaohui Zhong, Ann Arbor, MI (US); Ayush Pandey, Ann Arbor, MI (US); Wenzhe Zang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 287 days.

(21) Appl. No.: 16/071,441

(22) PCT Filed: Aug. 11, 2017

(86) PCT No.: PCT/US2017/046523
§ 371 (c)(1),
(2) Date: Jul. 19, 2018

(87) PCT Pub. No.: WO2019/032119
PCT Pub. Date: Feb. 14, 2019

(65) Prior Publication Data
US 2020/0200699 A1    Jun. 25, 2020

(51) Int. Cl.
*G01N 27/407* (2006.01)
*G01N 27/333* (2006.01)
(Continued)

(52) U.S. Cl.
CPC ..... *G01N 27/3335* (2013.01); *G01N 27/4045* (2013.01); *G01N 27/4075* (2013.01); *G01N 33/4972* (2013.01)

(58) Field of Classification Search
CPC .............. G01N 27/4071; G01N 27/4075
See application file for complete search history.

(56) References Cited

U.S. PATENT DOCUMENTS 5,788,826 A     8/1998 Nyberg
2006/0021881 A1    2/2006 Soundarrajan et al.
(Continued)

FOREIGN PATENT DOCUMENTS

CN     202471646 U  * 10/2012  ........... G01N 27/416
EP     3194072 A1     7/2017
(Continued)

OTHER PUBLICATIONS

EPO machine-generated English language translation of Li et al. CN 202471646 U (Year: 2012).*
(Continued)

*Primary Examiner* — Alexander S Noguerola
(74) *Attorney, Agent, or Firm* — Harness, Dickey & Pierce, P.L.C.

(57) ABSTRACT

Electrochemical sensors for the detection of select analytes are provided. The electrochemical sensors include a barrier layer having a substantially uniformed thickness disposed between a sensing layer and an ion exchange membrane. The barrier layer includes a two-dimensional nanomaterial. The barrier layer has a thickness of less than or equal to about 1 nm. The sensing layer has a thickness of less than or equal to about 10 nm. The sensing layer generates ions in response to select analytes. The barrier layer allows the generation ions to pass therethrough and travel into the ion exchange membrane. The barrier layer acts as a physical barrier to contaminants and larger molecules.

41 Claims, 14 Drawing Sheets

(51) Int. Cl.
   *G01N 27/404*   (2006.01)
   *G01N 33/497*   (2006.01)

(56) References Cited

U.S. PATENT DOCUMENTS

| | | |
|---|---|---|
| 2007/0108056 A1 | 5/2007 | Nyberg et al. |
| 2010/0193376 A1 | 8/2010 | Rius Ferrus et al. |
| 2012/0111093 A1 | 5/2012 | Brahim et al. |
| 2014/0027281 A1 | 1/2014 | Fodor et al. |
| 2015/0014167 A1* | 1/2015 | Dziallas ............... G01N 27/407 204/415 |
| 2015/0338368 A1 | 11/2015 | Viens et al. |
| 2016/0231267 A1 | 8/2016 | Swager et al. |
| 2017/0131230 A1 | 5/2017 | Papageorge et al. |

FOREIGN PATENT DOCUMENTS

| | | | | |
|---|---|---|---|---|
| WO | WO 2006071225 A1 * | 7/2006 | ............... | H01M 4/86 |
| WO | WO-2013-134738 A1 | 9/2013 | | |

OTHER PUBLICATIONS

Ramaswamy et al., "Degradation mechanism of perfluorinated protein exchange membrane under fuel cell operating conditions," Electrochimica Acta 53 (2008) 3279-3295 (Year: 2008).*

Liu et al. "Highly Durable Direct Methanol Fuel Cell with Double-Layered Catalyst Cathode," Journal of Nanomaterials vol. 2015, Article ID 963173, 8 pages (Year: 2015).*

International Search Report and Written Opinion issued in PCT/US2017/046523, dated Mar. 27, 2018; ISA/KR.

Byung Min Yoo, et al., "Graphene and Graphene Oxide and Their Uses in Barrier Polymers," Journal of Applied Polymer Science, Jan. 5, 2014, vol. 131 No. 1.

S. Guo et al "Platinum Nanoparticle Ensemble-On-Graphene Hybrid Nanosheet: One-Pot, Rapid Synthesis, and Used as New Electrode Material for Electrochemical Sensing" ACS nan, 4(7) (2010).

* cited by examiner

TWO-DIMENSIONAL MATERIAL BASED ION EXCHANGE MEMBRANE SENSORS

GOVERNMENT CLAUSE

This invention was made with government support under Grant No. 1548317 awarded by the National Science Foundation. The Government has certain rights in this invention.

CROSS REFERENCE TO RELATED APPLICATIONS

This application is a U.S. National Phase Application under 35 U.S.C. 371 of International Application No. PCT/US2017/046523 filed on Aug. 11, 2017. The entire disclosures of the above application are incorporated herein by reference.

FIELD

The present disclosure relates to ion exchange membrane sensors.

BACKGROUND

Electrochemical sensors are selective and sensitive and require relatively small sums of power for operation. Consequently, electrochemical sensors are widely used for chemical and biological detection. As seen in FIG. 1A, conventional electrochemical sensors 20 generally include two or more electrodes 22 disposed in a liquid electrolyte reservoir 24. The two or more electrodes 22 include a sensing electrode 26, a counter electrode 28, and a reference electrode 38. The reference electrode 38 is sandwiched between the sensing electrode 26 and the counter electrode 28. Suspect molecules or analytes 40 interact with the sensing electrode 26 inducing a redox or charge transfer reaction. The interaction of the sensing electrode 26 and the target analytes 40 products ions (e.g., protons, OH⁻) and counter charges (e.g., electrons). The charges (e.g., electrons) 30 flow through an external detection module 32 electrically coupled to the sensing electrode 26 and the counter electrode 28 to complete an external circuit. The ions 36 flow through the liquid electrolyte reservoir 24 to complete an internal circuit. Thus, a current proportional to the analyte concentration 38 flows between the electrodes 26, 28.

Liquid electrolyte reservoirs are impracticable where liquid leaks and spills are of concern. In certain instances, small packaged electrochemical gas sensors include a porous membrane soaked with a liquid electrolyte sandwiched between the electrodes. However, such sensors have limited life and are prone to errors resulting from drying of the electrolyte. In certain instances, liquid electrolyte reservoirs are replaced with solid electrolytes (e.g., ion exchange membrane (IEM)). Solid electrolytes are solid polymers that support the transportation of ions to complete the internal circuit.

Ion exchange membranes have been widely used in proton exchange fuel cells (PEFCs) 48. In various instances, as seen in FIG. 1B, an ion exchange membrane 50 is sandwiched between two thick electrode assemblies 52, 54. The first and second electrodes 52, 54 may include platinum (Pt) coated carbon-black electrode assemblies. The first and second electrodes 52, 54 are electrically coupled to an external module 56. Ion exchange membranes have also been used in limited gas sensing applications (e.g., breathalyzers). However, ion exchange membranes have not been widely used for such applications in part because of the high cost of platinum (Pt)/carbon-black electrodes and platinum-ruthenium (Pt—Ru)/carbon-black electrodes. Further, such ion exchange membrane devices need to be regularly recalibrated and used to avoid a loss of functionality. These ion exchange membrane devices have subpar signal quality and require a liquid reservoir for collecting by-products of the redox reaction.

This section provides background information related to the present disclosure which is not necessarily prior art.

SUMMARY

This section provides a general summary of the disclosure, and is not a comprehensive disclosure of its full scope or all of its features.

In various aspects, the present disclosure provides an exemplary electrochemical sensor for detection of analytes. The electrochemical sensor comprises an ion exchange membrane, a sensing layer, and a first barrier layer sandwiched therebetween. The ion exchange membrane has a first substantially planar surface that opposes a second substantially planar surface. The sensing layer has a substantially planar first surface that is substantially parallel with the first surface of the ion exchange membrane and is configured to generate ions in response to one or more select analytes. The first barrier layer comprises a nanomaterial.

In one variation, the ion exchange membrane is further defined as a proton exchange membrane having one or more of $SO_3^-$, $PO_4^-$, and $CO_3^-$ as the proton ion exchange group.

In one variation, the ion exchange membrane is further defined as an anion exchange membrane having quaternary ammonium ($NR_4^+$)/phosphonium ($PR_4^+$) or ammonium polysulfone groups as the anion exchange groups.

In one variation, the sensing layer has a thickness of less than or equal to about 10 nm.

In one variation, the sensing layer includes one or more materials selected from the group consisting of: platinum (Pt), tin (Sn), zinc (Zn), ruthenium (Ru), copper (Cu), titanium (Ti), chromium (Cr), gold (Au), silver (Ag), nickel (Ni), and combinations thereof.

In one variation, the first barrier layer has a thickness of less than or equal to about 1 nm.

In one variation, the first barrier layer includes one or more two-dimensional (2-D) materials selected from the group consisting of: graphene, transition metal dichalcogenides (TMDCs), phosphorene, silicene, germanene, stanene, borophene, and combinations thereof.

In one variation, the first barrier layer is a mesh network of one-dimensional (1-D) nanomaterials (e.g., nanotubes, nanowires).

In one variation the electrochemical sensor further comprises a functional layer and a second barrier layer. The functional layer has a substantially planar first surface that is substantially parallel with the second surface of the ion exchange membrane. The second barrier layer is sandwiched between the functional layer and the ion exchange membrane and comprises a nanomaterial. The functional layer and the second barrier layer are each configured to complete the ion generating reaction initiated within the sensing layer.

In one variation, the electrochemical sensor further comprises a detection module that is electrically coupled to at least one of the first barrier layer and the sensing layer and at least one of the second barrier layer and functional layer. The detection module is configured to detect flow of charge between the at least one of the first barrier layer and the sensing layer and the at least one of the second barrier layer and functional layer.

In one variation, the detection module is configured to measure a change in current or voltage traveling therethrough, and the measured change corresponds with an analyte concentration.

In one variation, a time-varying input is applied to the detection module using a battery coupled to an electronic circuit and an output change in one of an ac current, ac voltage, capacitance, heterodyne, or combination thereof is measured and correlated with an analyte concentration.

In one variation, the functional layer has a thickness of less than or equal to about 10 nm.

In one variation, the functional layer includes one or more materials selected from the group consisting of: platinum (Pt), tin (Sn), zinc (Zn), ruthenium (Ru), copper (Cu), titanium (Ti), chromium (Cr), gold (Au), silver (Ag), nickel (Ni), and combinations thereof.

In one variation, the second barrier layer has a thickness of less than or equal to about 1 nm.

In one variation, the second barrier layer includes one or more two-dimensional (2-D) materials selected from the group consisting of: graphene, transition metal dichalcogenides (TMDCs), phosphorene, silicene, germanene, stanene, borophene, and combinations thereof.

In one variation, the first barrier layer is a mesh network of one-dimensional (1-D) nanomaterials.

In one variation, the first surface of the ion exchange membrane includes a first portion that opposes a second portion and a third portion sandwiched therebetween. A first electrode is disposed on the first portion and a second electrode is disposed on the second portion.

In one variation, the sensing layer is substantially parallel with the third portion of the first surface of the ion exchange membrane.

In one variation, the electrochemical sensor further comprises a detection module that is electrically coupled to the first electrode and the second electrode. The detection module is configured to detect flow of charge between the first electrode and the second electrode.

In one variation, the detection module is configured to measure a change in current or voltage traveling therethrough, and the measured change corresponds with an analyte concentration.

In one variation, a time-varying input is applied to the detection module using a battery coupled to an electronic circuit and an output change in one of an ac current, ac voltage, capacitance, heterodyne, or combination thereof is measured and correlated with an analyte concentration.

In one variation, the electrochemical sensor further comprises a separator layer having a first substantially planar surface that opposes a second substantially planar surface. The first surface of the separator layer is substantially parallel with the second surface of the ion exchange membrane, and the separator is configured to collect the generated ions.

In one variation, the separator layer comprises a cellulose based polymer select from cellulose acetate, ethylene vinyl alcohol, polyamide based polymers, or combinations thereof.

In one variation, the electrochemical sensor further comprises a substrate layer having a substantially planar first surface that is substantially parallel with the second surface of the separator layer.

In other aspects, the present disclosure provides another exemplary electrochemical sensor for the detection of analytes. The electrochemical sensor comprises an ion exchange membrane, a first barrier layer, a sensing layer, a second barrier layer, and a functional layer. The ion exchange membrane has a first substantially planar surface that opposes a second substantially planar surface. The first barrier layer is disposed on the first surface of the ion exchange membrane and comprises a two-dimensional (2-D) nanomaterial. The sensing layer is disposed on an exposed substantially planar surface of the first barrier layer that opposes the first surface of the ion exchange membrane and is configured to generate ions in response to select analytes. The second barrier layer is disposed on the second surface of the ion exchange membrane and also comprises a two-dimensional (2-D) nanomaterial. The functional layer is disposed on the exposed substantially planar surface of the second barrier layer that opposes the second surface of the ion exchange membrane. The functional layer and the second barrier layer are each configured to complete the ion generating reaction initiated within the sensing layer.

In one variation, the ion exchange membrane is one of Nafion or Fumasep FKS/FKB/FKE/FAA/FAB/FAD/FAP/FAS.

In one variation, the sensing layer and the functional layer each have a thickness of less than or equal to about 10 nm.

In one variation, the sensing layer and the functional layer each include one or more materials selected from the group consisting of: platinum (Pt), tin (Sn), zinc (Zn) ruthenium (Ru), copper (Cu), titanium (Ti), chrome (Cr), gold (Au), silver (Ag), nickel (Ni), and combinations thereof.

In one variation, the first and second barrier layers each have a thickness of less than or equal to about 1 nm.

In one variation, the first and second barrier layers each include one or more two-dimensional materials selected from the group consisting of: graphene, transition metal dichalcogenides (TMDCs), phosphorene, silicene, and combinations thereof.

In one variation, the electrochemical sensor further comprises a detection module that is electrically coupled to at least one of the first barrier layer and the sensing layer and at least one of the second barrier layer and functional layer. The detection module is configured to measure a change in current or voltage traveling therethrough and the measured change corresponds with an analyte concentration.

In other aspects, the present disclosure provides another exemplary electrochemical sensor for the detection of analytes. The electrochemical sensor comprises an ion exchange membrane, a barrier layer, a sensing layer, a first electrode, a second electrode, a separator layer, and a substrate layer. The ion exchange membrane has a first substantially planar surface that opposes a second substantially planar surface. The first substantially planar surface has a first portion distal from a second portion and a third portion sandwiched therebetween. The barrier layer is disposed on the third portion of the first surface of the ion exchange membrane. The barrier layer comprises a two-dimensional (2-D) nanomaterial. The sensing layer is disposed on an exposed substantially planar surface of the barrier layer that opposes the third portion of the first surface of the ion exchange membrane. The sensing layer is configured to generate ions in response to select analytes. The first electrode is disposed on the first portion of the first surface of the ion exchange membrane. The second electrode is disposed on the second portion of the first surface of the ion exchange membrane. The separator layer is disposed on the second surface of the ion exchange membrane and is configured to collect the generate ions. The substrate layer is disposed on an exposed substantially planar surface of the separator that opposes the second surface of the ion exchange membrane.

In one variation, the ion exchange membrane is one of Nafion or Fumasep FKS/FKB/FKE/FAA/FAB/FAD/FAP/FAS.

In one variation, the sensing layer has a thickness of less than or equal to about 10 nm.

In one variation, the sensing layer and the functional layer each include one or more materials selected from the group consisting of: platinum (Pt), tin (Sn), zinc (Zn) ruthenium (Ru), copper (Cu), titanium (Ti), chrome (Cr), gold (Au), silver (Ag), nickel (Ni), and combinations thereof.

In one variation, the barrier layer has a thickness of less than or equal to about 1 nm.

In one variation, the barrier layer includes one or more two-dimensional materials selected from the group consisting of: graphene, transition metal dichalcogenides (TMDCs), phosphorene, silicene, and combinations thereof.

In one variation, the separator layer comprises separator layer comprises a cellulose based polymer select from cellulose acetate, ethylene vinyl alcohol, polyamide based polymers, or combinations thereof.

In one variation, the electrochemical sensor further comprises a detection module that is electrically coupled to at least one of the first barrier layer and the sensing layer and at least one of the second barrier layer and functional layer. The detection module is configured to measure a change in current or voltage traveling therethrough and the measured change corresponds with an analyte concentration.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Electrochemical sensors generally include a sensing material that reacts with a chemical of interest (e.g., analyte) in a manner that produces an electrical charge. By setting up a circuit and measuring this charge, the concentration of the chemical of interest can be determined. Such chemical sensing has wide array of applications, including in environmental monitoring, biochemical defense and warfare, healthcare applications, and automotive and industrial applications for monitoring gas concentration. However, as noted above, electrochemical sensors have been met with limited success because of issues such as material costs, signal quality and measurement accuracy, high operational temperatures and power consumption (e.g., for metal-oxide based electrochemical sensors), and limited life. Accordingly, the present technology provides an electrochemical sensor including a barrier and/or conductive layer comprising a two-dimensional nanomaterial (e.g., graphene). The barrier layer has a substantially uniformed thickness. The barrier layer is disposed between a sensing layer and an ion exchange member. The barrier layer allows for a reduction in the size of electrochemical sensors (e.g., thin). Further, the barrier layer may have high conductivity, reduce signal noise (e.g., uniformity), protect internal layers from contamination, and increase the flexibility and wearability of electrochemical sensors.

Figure 1A:
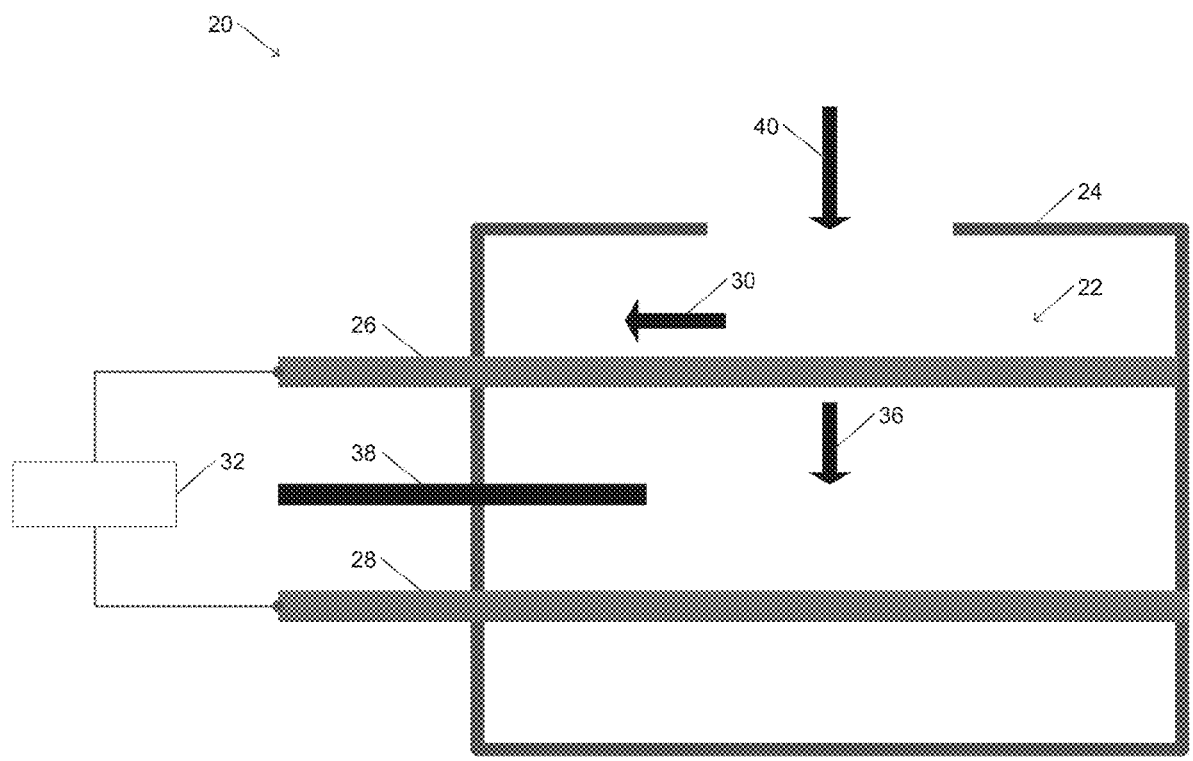
FIG. 1A is a schematic showing a conventional electrochemical sensor, including an electrode device in a liquid electrolyte reservoir.
Figure 1B:
FIG. 1B is a schematic showing a conventional fuel cell, including an ion exchange membrane.
Figure 2:
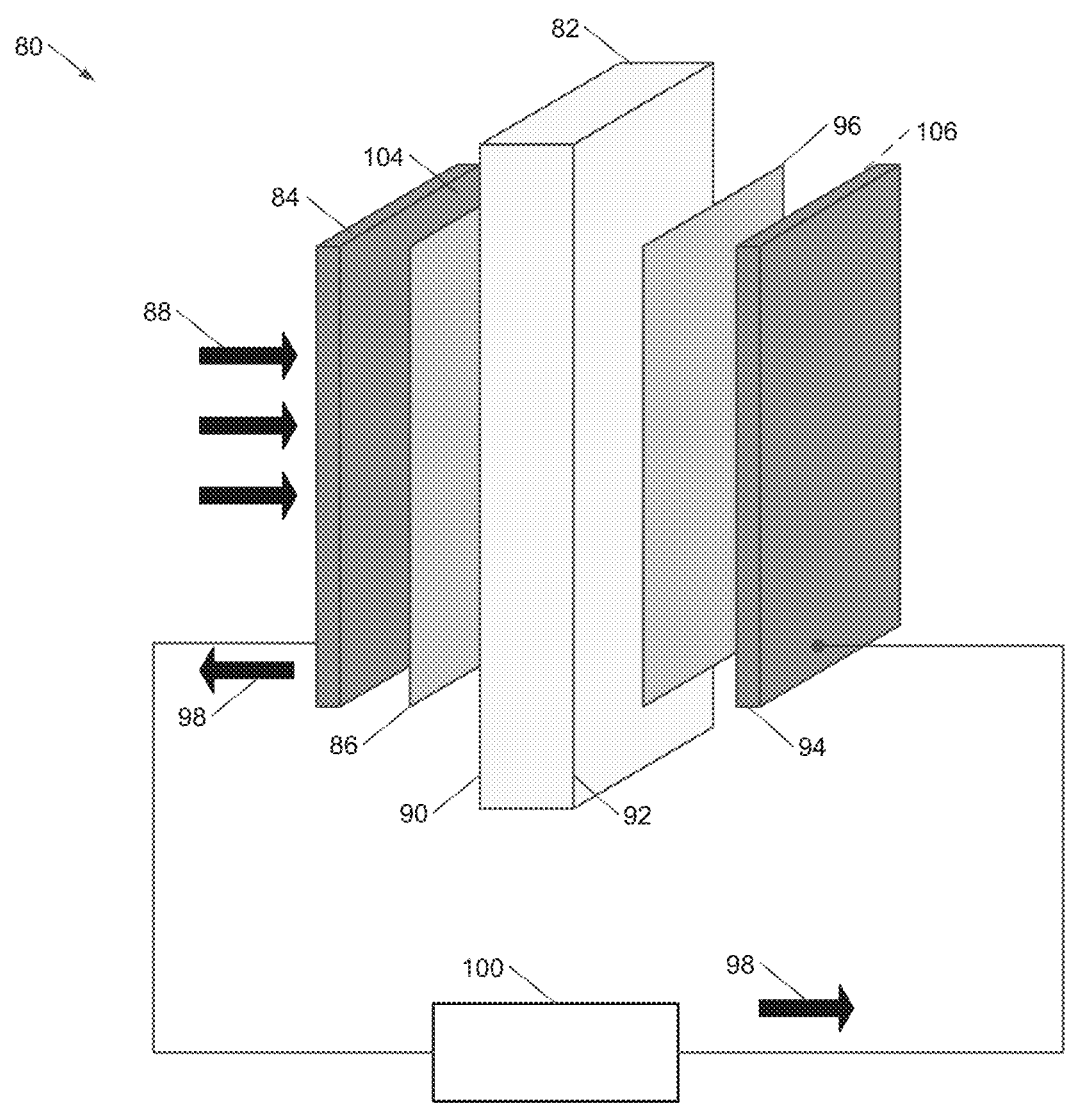
FIG. 2 is a schematic showing an example two-dimensional electrochemical sensor for the detection of an analytes prepared in accordance with certain aspects of the present disclosure.

FIG. 2 provides an example illustration of a two-dimensional (2-D) electrochemical sensor 80 for the detection of analytes 88 (e.g., ethanol vapors). Electrochemical sensor 80 comprises an ion exchange membrane (IEM) or electrolyte membrane 82, a sensing or functionalization coat or layer 84, and a barrier coat or layer 86 having a substantially uniformed thickness. The ion exchange membrane 82 has a first substantially planar surface 90 opposing a second substantially planar surface 92. In one embodiment, a substantially planar first surface 104 of the sensing layer 84 is substantially parallel with the first surface 90 of the ion exchange membrane 82. In such instances, the barrier layer 86 is sandwiched between the sensing layer 84 and the ion exchange membrane 82. The barrier layer 86 is sandwiched between the first surface 104 of the sensing layer 84 and the second surface 92 of the ion exchange membrane 82. In another embodiment, the barrier layer 86 is disposed on the surface 90 of the ion exchange membrane 82. In such instances, the sensing layer 84 is disposed on the exposed surface of the barrier layer 86 opposing the first surface 90 of the ion exchange membrane 82. The first surface 104 of the sensing layer 84 interfaces with the barrier layer 86.

As illustrated in FIG. 2, in certain instances, the electrochemical sensor 80 includes a second functional layer 94 and a second barrier layer 96 having a substantially uniformed thickness. In one embodiment, a substantially planar first surface 106 of the second functional layer 94 may be substantially parallel with the second surface 92 of the ion exchange membrane 82. In such instances, the second barrier layer 96 is sandwiched between the second functional layer 94 and the ion exchange membrane 82. The second barrier layer 96 is sandwiched between the first surface 106 of the second functional layer 94 and the second surface of the ion exchange membrane 82. In another embodiment, the second barrier layer 96 is disposed on the second surface of the ion exchange membrane 82. In such instances, the second functional layer 94 is disposed on the exposed surface of the second barrier layer 96 opposing the second surface 92 of the ion exchange membrane 82. The first surface 106 of the second functional layer 94 interfaces with the barrier layer 96.

The ion exchange membrane 82 is selected to achieve selective transmission of ions. In one embodiment, the ion exchange membrane 82 is a cation or proton exchange membrane. Cation exchange membranes have fixed anionic groups and mobile cations (e.g., $H^+$). An example cation exchange membrane is Nafion. In various instances, cation exchange membranes may have sulfur trioxide ($SO_3^-$), phosphate ($PO_4^-$), carbonate ($CO_3^-$), or a combination thereof as proton ion exchange groups. In another embodiment, the ion exchange membrane 82 is an anion exchange membrane. Anion exchange membranes have fixed cationic groups and mobile anions (e.g., $OH^-$). Example anion exchange membranes include Fumasep FAA or FAP. In various instances, anion exchange membranes may have quaternary ammonium ($NR_4^+$)/phosphonium ($PR_4^+$), ammonium polysulfone groups, or a combination thereof as anion exchange groups. In either embodiment, the ion exchange membrane 82 is a solid electrolyte for the electrochemical sensor 80. The ion exchange membrane may have a thickness of about 100-300 μm.

The first sensing layer 84 and the second functional layer 94 are selected to achieve selective detection. In various embodiments, the first sensing layer 84 and the second functional layer 94 include metal and/or semiconducting nanoparticles or thin films, polymers, dyes, surface assembled layers, receptors, or combinations thereof. Materials of the first sensing layer 84 and the second functional layer 94 may be selected from the group consisting of: platinum (Pt), tin (Sn), zinc (Zn), ruthenium (Ru), copper (Cu), titanium (Ti), chromium (Cr), gold (Au), silver (Ag), nickel (Ni), and combinations thereof. The first sensing layer 84 and the second functional layer 94 may each have a thickness less than or equal to about 10 nm.

The first sensing layer 84 is configured to interact with the target analyte(s) or molecule(s) 88. The interaction of the first sensing layer 84 and the target analyte 88 generates ions (not shown) and counter charges 98. For example, in one embodiment, the first sensing layer 84 may interaction with the target analyte 88 via a redox reaction to generate ions relating to or depending from the target analyte 88. In another embodiment, the first sensing layer 84 may interact with the target analyte 88 via another charge transfer reaction to generate ions relating to or depending from the target analyte 88. In either embodiment, the first sensing layer 84 rejects interferents or contaminants. The second functional layer 94 is configured to complete the ion generating interaction of the first sensing layer 84. In certain instances, the first sensing layer 84 and/or the second functional layers 94 may include a pre-concentrator functional layer to enhance the sensitivity of the electrochemical sensor 80.

The barrier layers 86, 96 are also selected to achieve sensitive detection. The first and second barrier layers 86, 96 comprise a highly conductive material. For example, in one embodiment, the first and second barrier layers 86, 96 each comprise a two-dimensional (2-D) nanomaterial. The two-dimensional (2-D) nanomaterial may be graphene, transition metal dichalcogenides (TMDCs), phosphorene, silicene, germanene, stanene, borophene, or combinations thereof. In another embodiment, the first and second barrier layers 86, 86 may include similar two-dimensional (2-D) nanomaterials. In another embodiment, the first and second barrier layers 86, 96 each comprise a mesh network of one-dimensional (1-D) nanomaterial(s). The one-dimensional nanomaterial(s) may be carbon nanotubes, nanowires, or combinations thereof. In either embodiment, the first and second barrier layers 86, 96 each have a thickness less than or equal to about 1 nm and are flexible. The two-dimensional (2-D) and one-dimensional (1-D) nanomaterials have substantially perfect lattice structures.

The first and second barrier layers 86, 96 having substantially perfect lattice structures and high uniformity allow for a reduction in the thickness of the first sensing layer 84 and/or the second functional layer 94. Thus, the first and second barrier layers 86, 96 allow for a substantial reduction in the overall costs of the electrochemical sensor 80. For example, a first sensing layer 84 having a thickness of about 10 nm has a platinum (Pt) loading requirement of about 0.2 pg/cm$^2$, while a conventional electrode has a loading requirements of platinum (Pt) on carbon (C) of about 1 mg/cm$^2$ and 25 pg/cm$^2$ in the absence of a carbon (C) backing. Thus, electrochemical sensor 80 has an improvement factor of at least $10^9$. Further, by reducing the catalyst amount and eliminating the conductive carbon cloth backing seen in commercially available membrane sensors, the total device size (e.g. electrochemical sensor 80) is reduced from a thickness of about 1-2 mm to about 100-300 μm.

The first and second barrier layers 86, 96 form a protective encapsulation of the ion exchange membrane 82. The first and second barrier layers 86, 96 are substantially impervious to gas molecules. Thus, the first and second barrier layers 86, 96 protect the ion exchange membrane 82 from dehydration and contamination. In particular, the first and second barrier layers 86, 96 allows for the transport of the generated ions or charges through the ion exchange membrane 82 while providing a physical barrier to large molecules and contaminants. In this fashion, the first and second barrier layers 86, 96 improve the life of the electrochemical sensor. For example, the first and second barrier layers 86, 96 reduce the number of necessary recalibrations. Further, the nanomaterials of the first and second barrier layers 86, 96 are sensitive to external environmental changes. Therefore, the barrier layers 86, 96 improve overall sensing capabilities of the electrochemical sensor 80.

The interaction of the first sensing layer 84 and the target analyte 88 generates ions (not shown) and counter charges 98. The first barrier layer 86 allows the ions (e.g., $H^+$, $OH^-$) to pass therethrough into the ion exchange membrane 82. The ions travel through the ion exchange membrane 82 to the second barrier layer 96. The second barrier layer 96 completes the electrical circuit as it collects the ions causing the ions to interact with the second functional layer 94 to produce gaseous products (e.g., $O_2$, $H_2O$). The counter charges 98 (e.g., electrons) flow through an external detection or measurement module or circuit 100. The detection module 100 is configured to detect the flow of charge therethrough.

In one embodiment, the external detection module 100 is electrically coupled to (i) the first sensing layer 84 and (ii) the second functional layer 94. In another embodiment, the external detection module 100 is electrically coupled to (i) the first sensing layer 84 and (ii) the second barrier layer 96. In another embodiment, the external detection module 100 is electrically coupled to (i) the first barrier layer 86 and (ii) the second functional layer 94. In still another embodiment, the external detection module 100 is electrically coupled to (i) the first barrier layer 86 and the (ii) second barrier layer 96. In yet another embodiment, the external detection module 100 is electrically coupled to (i) both the first sensing layer 84 and the first barrier layer 86 and (ii) both the second functional layer 94 and the second barrier layer 96. In each embodiment, the electrochemical sensor 80 is a two-terminal device. A bias voltage generally need not be applied to the electrochemical sensor 80. However, in some embodiments, a DC bias voltage (e.g., less than or equal to about 1V) may be applied to enhance the sensor 80 signal.

Analyte concentration is determined by measuring the flow of charge 98 through the detection module 100. In one embodiment, a change in voltage and/or current may be measured and correlated with the analyte 88 concentration. In another embodiment, a time-varying input (e.g., ac-sinusoidal, pulse, triangular excitation) may be used and an output change in ac current and/or voltage, capacitance, heterodyne, or a combination thereof measured and correlated with the analyte 88 concentration.

Figure 3:
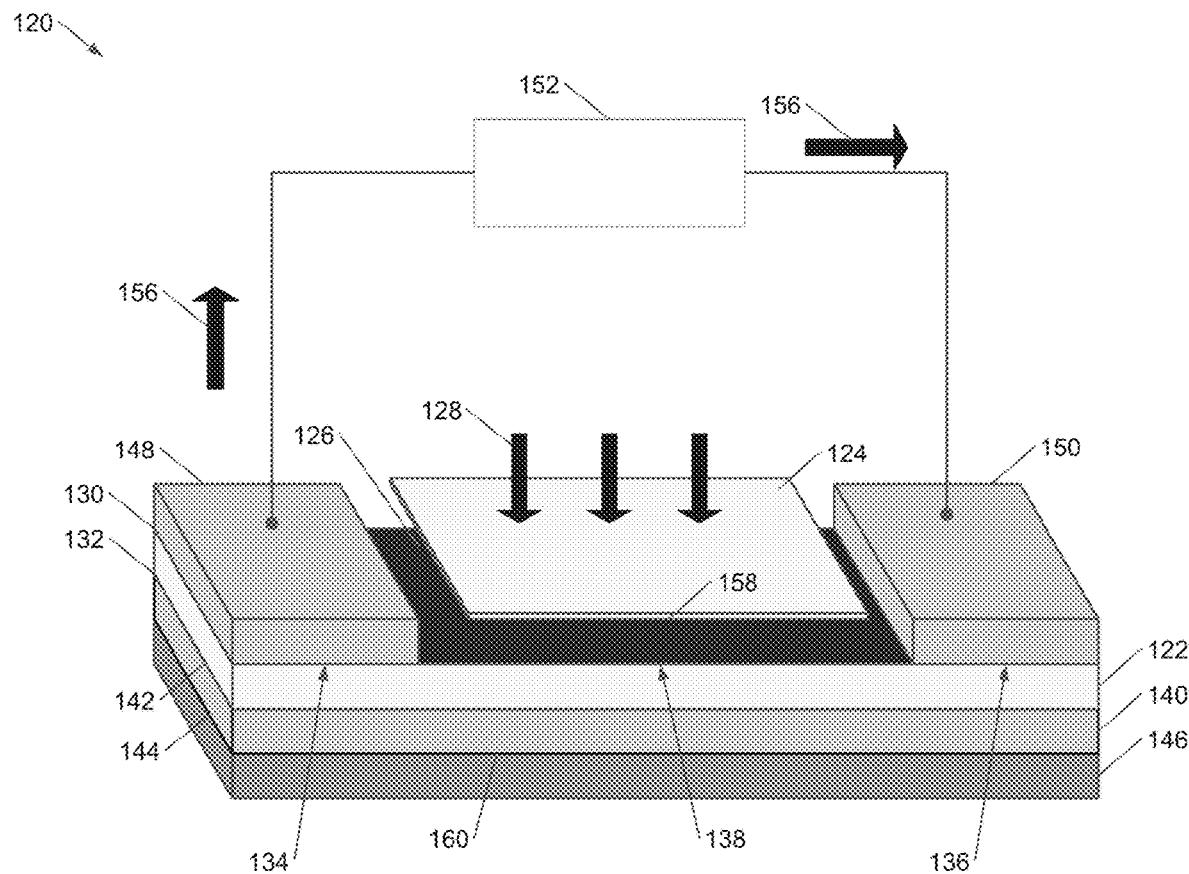
FIG. 3 is a schematic showing an example planar electrochemical sensor for the detection of analytes prepared in accordance with certain aspects the present disclosure.

FIG. 3 depicts an alternative embodiment. In this alternative embodiment, electrochemical sensor 120 has a planar arrangement. Electrochemical sensor 120 comprises an ion exchange membrane 122, a sensing layer 124, and a barrier layer 126 having a substantially uniformed thickness. The ion exchange membrane 122 has a first substantially planar surface 130 opposing a second substantially planar surface 132. The first surface 130 of the ion exchange membrane 122 has a first portion 134 distal from a second portion 136 and a third portion 138 sandwiched therebetween.

In one embodiment, a substantially planar first surface 158 of the sensing layer 124 is substantially parallel with the third portion 138 of the first surface 130 of the ion exchange membrane 122. In such instances, the barrier layer 126 is sandwiched between first surface 158 of the sensing layer 124 and the third portion 138 of the first surface 130 of the ion exchange membrane 122. In another embodiment, the barrier layer 126 is disposed on the third portion 138 of the first surface 130 of the ion exchange membrane 122. In such instances, the sensing layer 124 is disposed on an exposed surface of the barrier layer 126 opposing the first surface 130 of the ion exchange membrane 122. The first surface of the sensing layer 124 interfaces with the barrier layer 126. In another embodiment, the sensing layer 124 extends from a first electrode 148 to a second electrode 150 forming a connection therebetween.

In various instances, as illustrated, electrochemical sensor 120 further includes a separator or separating layer 140. The separator 140 has a first substantially planar surface 142 opposing a second substantially planar surface 144. In one embodiment, the first surface 142 of the separator 140 is substantially parallel with the second surface 132 of the ion exchange membrane 122. In another embodiment, the separator 140 is disposed on the ion exchange membrane 122. The first surface 142 of the separator 140 is disposed on the second surface 132 of the ion exchange membrane 122. The separator 140 may comprise cellulose based polymers, including cellulose acetate, ethylene vinyl alcohol, polyamide based polymers, or combinations thereof.

Further, in certain instances, the electrochemical sensor 120 further includes a substrate layer 146. In one embodiment, a substantially planar first surface 160 of the substrate layer 146 is substantially parallel with the second surface 144 of the separator 140. In other instances, the substrate layer 146 is disposed on the separator 140. The first surface 160 of the substrate layer 146 is disposed on the second surface 144 of the separator 140. The substrate 146 may comprise a flexible plastic (e.g., PET, PEN, PDMS, silicone); a conventional substrate such as silicon (Si), silicon-oxide on silicon (Si) (e.g., $SiO_2$/Si), or silicon nitride on silicon (Si) (e.g., $Si_3N_4$/Si); or other paper substrates commonly used in electronics. In various instances, the components (e.g., 122, 124, 126, 140) of electrochemical sensor 120 may be spun-on or spin-coated on the substrate 146.

Similar to first sensing layers 84, sensing layer 124 is configured to interact with the target analytes(s) or molecule(s) 128. The interaction of the sensing layer 124 and the target analyte(s) 128 generates ions (not shown) and relating or depending counter charges (e.g., electrons) 156. The barrier layer 126 allows the generated ions (e.g., $H^+$, $OH^-$) to pass therethrough and into the ion exchange membrane 122. The barrier layer 126 provides a physical barrier to larger molecules and contaminants. The generated ions that pass through the ion exchange membrane 122 are collected within the separator 140. The generated ions may react with $O_2$ or $OH^-$ bonds within the separator 140 to form water ($H_2O$). The generated byproducts are retained within the separator 140.

In one embodiment, first and second electrodes 148, 150 are disposed on the first and second portions 134, 136 of the first surface 130 of the ion exchange membrane 122. A first electrode 148 is disposed on the first portion 134 of the first surface 130 of the ion exchange membrane 122. A second electrode 150 is disposed on the second portion 136 of the first surface 130 of the ion exchange membrane 122. In another embodiment, the first and second electrodes 148, 150 are substantially parallel with the first and second portions 134, 136 of the first surface 130 of the ion exchange membrane 122. The first electrode 148 is substantially parallel with the first portion 134 of the first surface 130 of the ion exchange membrane 122. The second electrode 150 is substantially parallel with the second portion 136 of the first surface 130 of the ion exchange membrane 122. In either embodiment, the first and second electrodes 148, 150 may include gold (Au), titanium (Ti), palladium (Pd), chrome (Cr), silver (Ag), platinum (Pt), carbon (C), gold-chloride (AuCl), or a combination thereof.

A detection module 152 is electrically coupled to the first and second electrodes 148, 150. The counter charges 156 (e.g., electrons) flow through the external detection module 152. The detection module 152 is configured to detect flow of charge 156 therethrough. Analyte concentration is determined by measuring the flow of charge 165 through the detection module 152. In one embodiment, a change in voltage and/or current may be measured and correlated with the analyte 128 concentration. In another embodiment, a time-varying input (e.g., ac-sinusoidal, pulse, triangular excitation) may be used and an output change in ac current and/or voltage, capacitance, heterodyne, or a combination thereof measured and correlated with the analyte 128 concentration.

In certain instances, electrochemical sensor 120 may further include a reference electrode (not shown). The reference electrode may be disposed adjacent the ion exchange membrane 122. In one embodiment, the reference electrode is sandwiched between the ion exchange membrane 122 and the separator 140. The reference electrode is disposed adjacent the second surface 132 of the ion exchange membrane 122 and the first surface 142 of the separator 140. A first substantially planar surface of the reference electrode may be substantially parallel with the second surface 132 of the ion exchange membrane 122. A second substantially planar surface of the reference electrode may be substantially parallel with the first surface 142 of the separator 140. The reference electrode may increase the stability of the electrochemical sensor 120. Increasing the stability of the electrochemical sensor 120 increases its sensitivity and functionality. The reference electrode may have a composition similar to electrodes 148 and 150. In one embodiment, the detection module 152 is electrically coupled to the reference electrode.

In either embodiment (e.g., FIG. 2 and FIG. 3), the respective barrier layers 86, 96, 126 provide a substrate whereon the respective sensing or functionalization layers 84, 94, 124 may be disposed. Consequently, the thickness of each sensing layers 84, 94, 124 may be reduced allowing for a reduction in material costs (e.g., platinum (Pt)) while maintaining high surface conductivity and uniformity. Absent the barrier layer 86, 96, 126 the materials comprising the sensing layers 84, 94, 134 tend to agglomerate and form inefficient clusters at low thicknesses. Further, reducing the thickness of each electrochemical sensors 80, 120 increases the flexibility of the sensors 80, 120 thereby increasing the available sensor 80, 120 applications.

Embodiments of the present technology are further illustrated through the following non-limiting examples.

EXAMPLE 1

FIGS. 4A-4G compare a first two-dimensional electrochemical sensor 180 having barrier layers 186, 190 prepared in accordance with the present disclosure to a second two-dimensional electrochemical sensor 210 not having barrier layers.

Figure 4A:
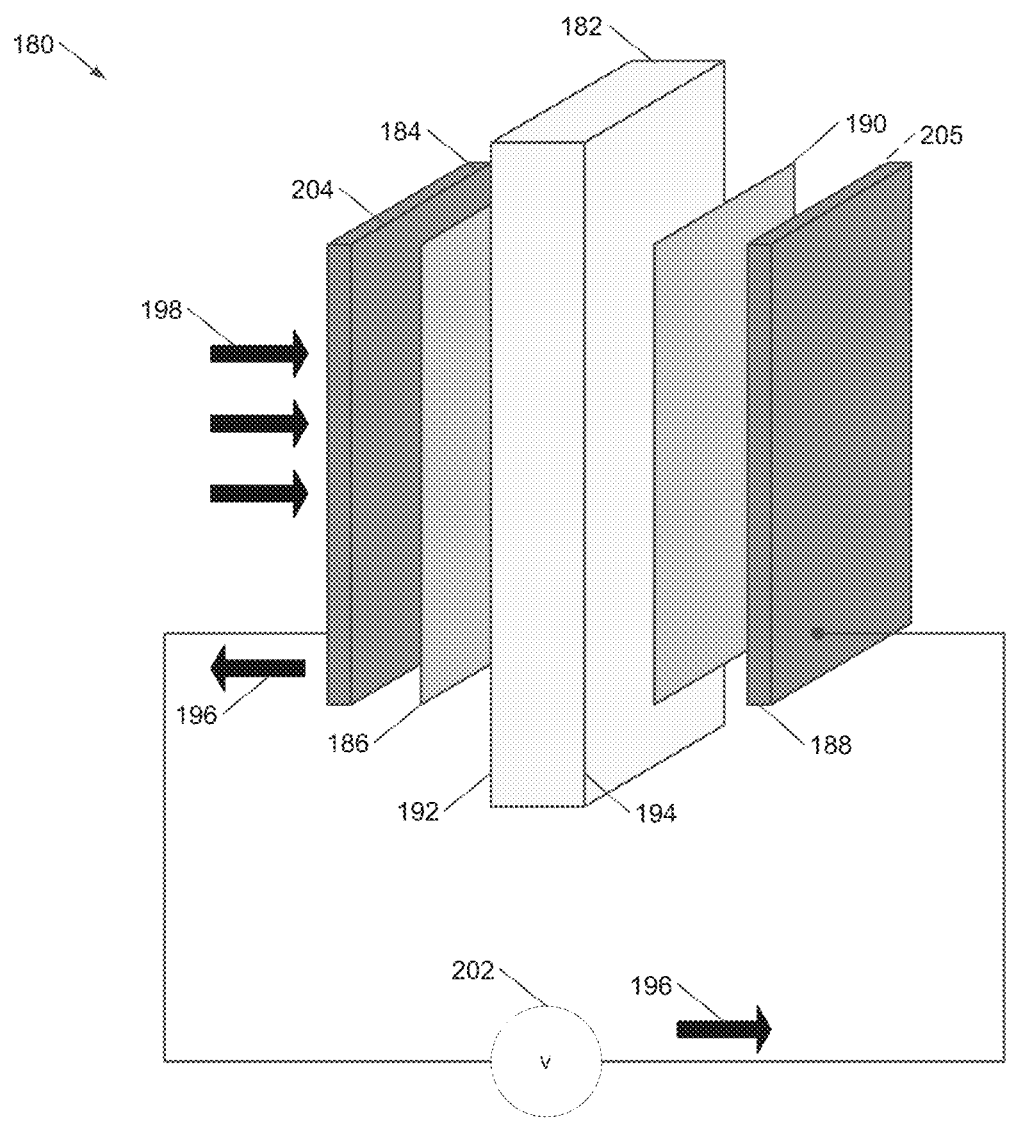
FIG. 4A is a schematic showing another example two-dimensional electrochemical sensor for the detection of analytes prepared in accordance with certain aspects of the present disclosure.

FIG. 4A illustrates the first electrochemical sensor 180. Electrochemical sensor 180 has a proton exchange membrane 182, a first sensing layer 184, a second functional layer 188, and first and second barrier layers 186, 190. The proton exchange membrane 182 comprises Nafion-117. The proton exchange membrane 182 has a first substantially planar surface 192 opposing a second substantially planar surface 194. The first sensing layer 184 is disposed adjacent the ion exchange membrane 182. A first substantially planar surface 204 of the first sensing layer 184 is disposed adjacent the first surface 192 of the ion exchange membrane 182. The first sensing layer 184 is configured to generate ions (not shown) and counter charges 196 in response to the analyte, ethanol vapors 198. The first barrier layer 186 is disposed between the first surface 204 of the first sensing layer 184 and first surface 192 of the ion exchange membrane 182. The first barrier layer 186 is a graphene layer having a one-atom thickness, which allows the passage of the generated ions therethrough.

A substantially planar first surface 206 of the second functional layer 188 is disposed adjacent the second surface 194 of the ion exchange membrane 182. The second functional layer 188 is configured to complete the ion generating reaction initiated by the first sensing layer 184. The second barrier layer 190 is disposed between the first surface 206 of the second functional layer 188 and the second surface of the ion exchange membrane 182. The second barrier layer 190 together with the first barrier layer 186 form a protective barrier around the ion exchange membrane 182. The second barrier layer 190 is a graphene layer having a one-atom thickness.

The substantially perfect planar lattice of graphene comprising the first and second barrier layers 186, 190 allows the thickness of the first sensing layer 184 and the second functional layer 188 to be minimized. The first sensing layer 184 and the second functional layer 188 have thickness of about 10 nm, optionally 5 nm. The first sensing layer 184 and the second functional layer 188 include platinum (Pt) and tin (Sn). Thus, minimizing the necessary thickness of both the first sensing layer 184 and the second functional layer 188 reduces the overall costs of the electrochemical cell 180. The first sensing layer 184 and the second functional layer 188 are electrically coupled to a voltmeter 202, which measures a flow of charge 196 (e.g., electrons) therethrough.

The first sensing layer 184 interacts with the ethanol vapor analytes 198 and oxidizes the ethanol:

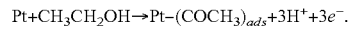

$$Pt + CH_3CH_2OH \rightarrow Pt-(COCH_3)_{ads} + 3H^+ + 3e^-.$$

Tin (Sn) is used in combination with platinum (Pt) to assist in the recovery of the platinum (Pt) following oxidation of the ethanol:

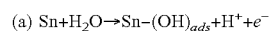

(a) $Sn + H_2O \rightarrow Sn-(OH)_{ads} + H^+ + e^-$ and

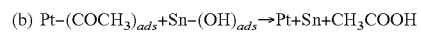

(b) $Pt-(COCH_3)_{ads} + Sn-(OH)_{ads} \rightarrow Pt + Sn + CH_3COOH$

The generated protons (H$^+$) migrate through the first and second barrier layer 186, 190 and the ion exchange membrane 182 into the second functional layer 188. The hydrophobic nature of graphene repels water from the surface of the membrane allowing only protons (H$^+$) to pass therethrough. In the second functional layer 188, the protons (H$^+$) react with oxygen (O$_2$):

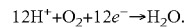

$$12H^+ + O_2 + 12e^- \rightarrow H_2O.$$

The circuit is completed by the flow of the electrons (e) 196 through the external circuit 200.

Figure 4B:
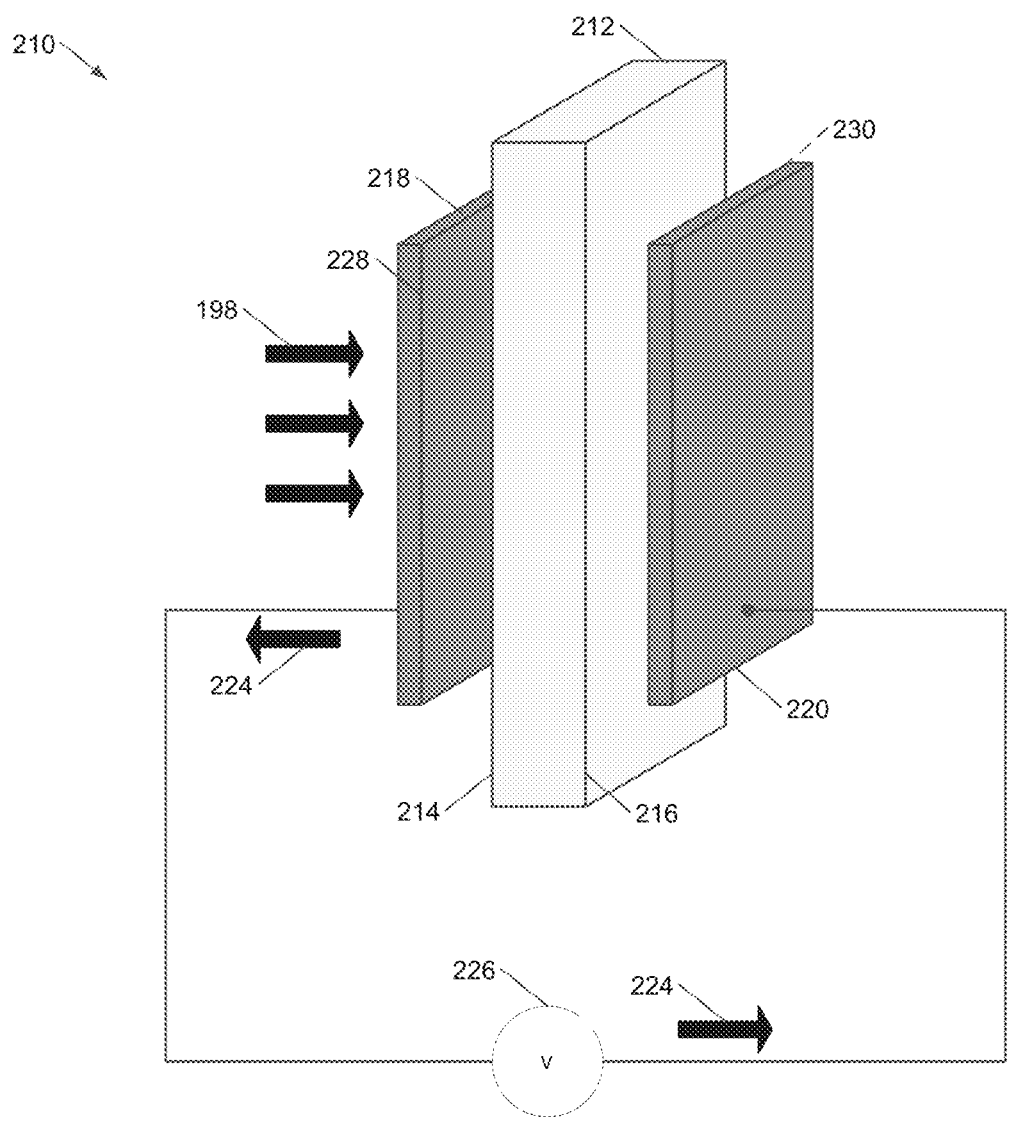
FIG. 4B is a schematic showing a conventional two-dimensional electrochemical sensor.

FIG. 4B illustrates the second electrochemical cell 210. Electrochemical cell 210, similar to electrochemical cell 180, includes an ion exchange membrane 212 including Nafion-117. The ion exchange membrane 212 has a first substantially planar surface 214 opposing a second substantially planar surface 216. A first substantially planar surface 228 of the first sensing layer 218 is disposed adjacent the first surface 214 of the ion exchange membrane 212. A first substantially planar surface 230 of a second functional layer 220 is disposed adjacent the second surface 216 of the ion exchange membrane 212.

The first sensing layer 218 and the second functional layer 220 include platinum (Pt) and tin (Sn). The first sensing layer 218 and the second functional layer 220 each have a thickness of about 5 nm. Absent the barrier layer (e.g., 186, 190) platinum (Pt) and tin (Sn) tend to form inefficient clusters. The first sensing layer 218 and the second functional layer 220 are electrically coupled to a voltmeter 226, which measures a flow of charge 224 (e.g., electrons) therethrough.

Figure 4C:
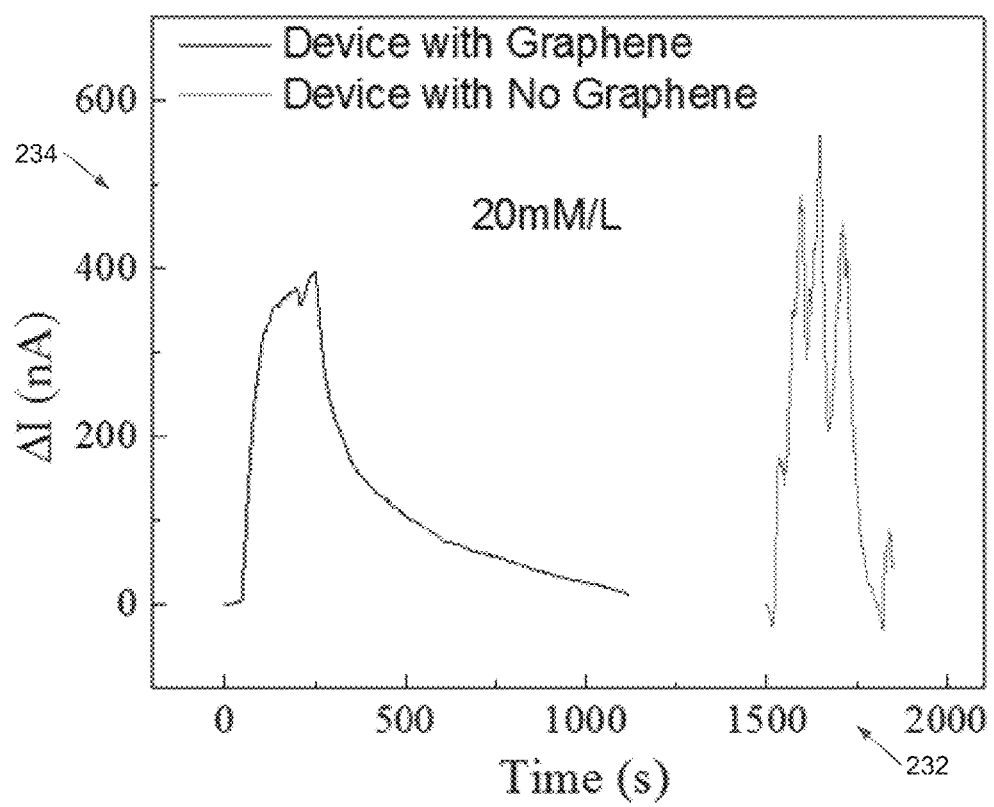
FIG. 4C illustrates the signal noise of the electrochemical sensor of FIG. 4A with respect to the signal noise of the electrochemical sensor of FIG. 4B.

A voltage of 1V was applied to the first and second electrochemical sensors 180, 210. The respective currents were then recorded for each sensor 180, 210 with respect to time. The measured currents were used to evaluate the response to vapors 198 from headspace of different concentrations of ethanol in water. The first and second electrochemical cells 180, 210 were exposed to vapors from ethanol in water for 200 seconds. As seen in FIG. 4C, the noise level 234 of electrochemical sensor 210 not including graphene layers is larger than the noise level 236 of electrochemical sensor 180 including the graphene layers 186, 190. The y-axis 234 of FIG. 4C depicts a change in current (ΔI) in nanoamperes (nA). The x-axis 232 of FIG. 4C depicts time in seconds (s).

Figure 4D:
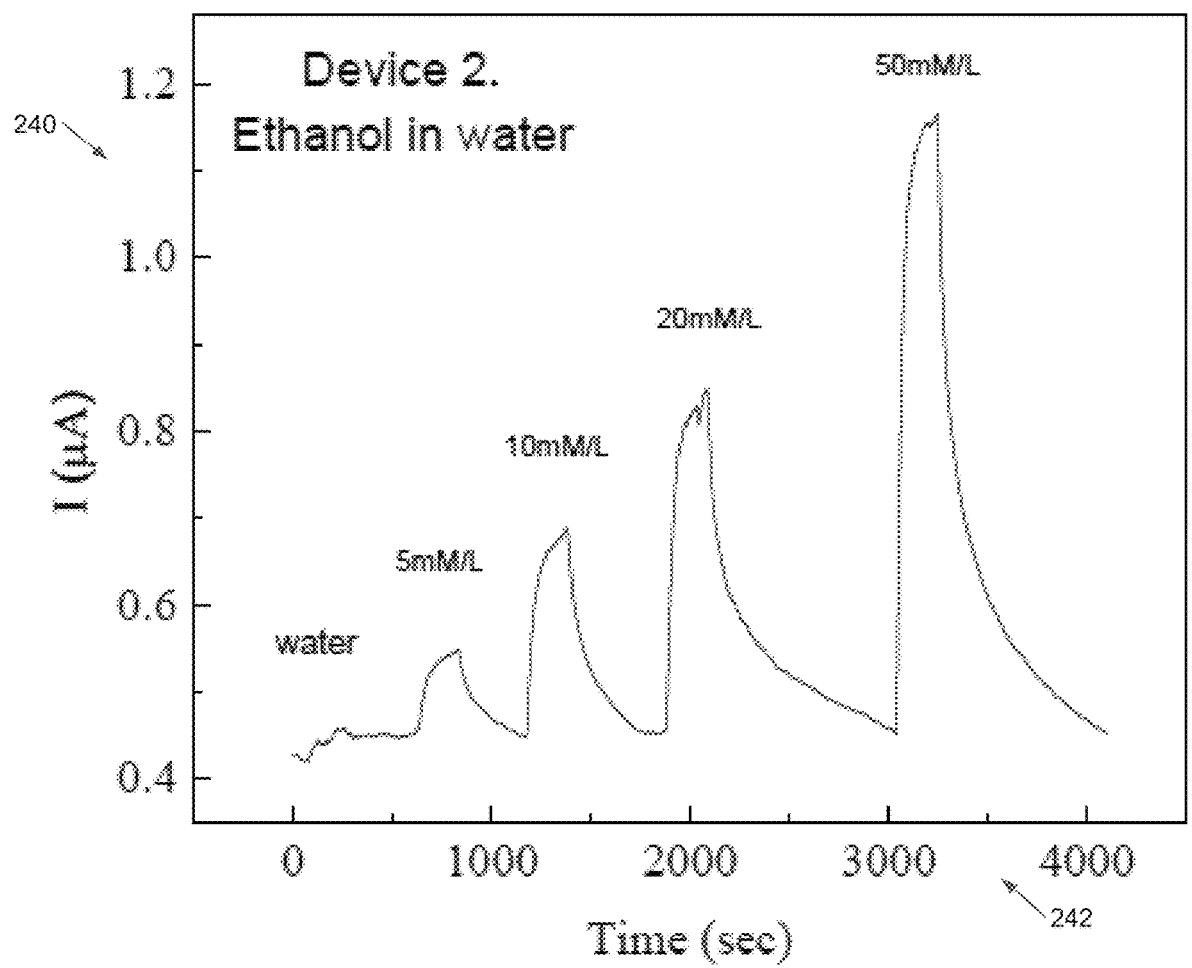
FIG. 4D illustrates the detection of ethanol vapors by the electrochemical sensor of FIG. 4A.

Further, as seen in FIG. 4D, the first electrochemical sensor 180, including first and second barrier layers 184, 190, detects ethanol vapors from as low as 5 mM ethanol in water. Further, as illustrated, the first electrochemical sensor 180 responds quickly to the ethanol in water (e.g., $t_{0\text{-}90\%}^{5mM}=179$ s; $t_{0\text{-}90\%}^{10mM}=116$ s; $t_{0\text{-}90\%}^{20mM}=106$ s; $t_{0\text{-}90\%}^{50mM}=79.1$ s). The y-axis 240 of FIG. 4D depicts current (I) in microamperes (μA). The x-axis 242 of FIG. 4D depicts time in seconds (s).

Figure 4E:
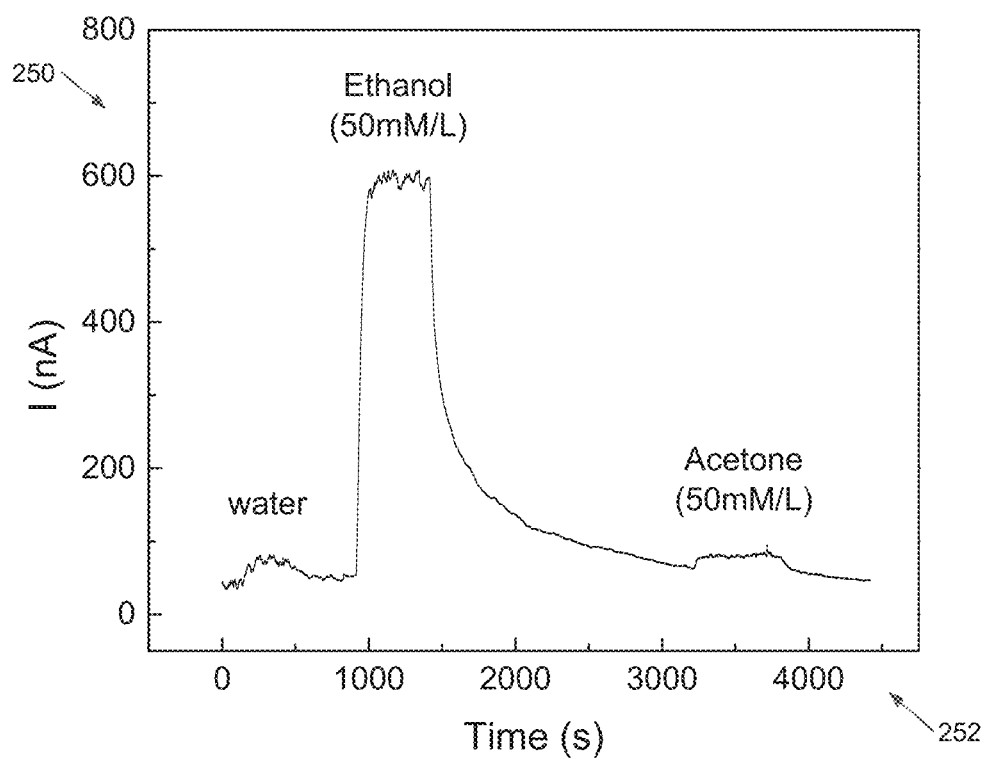
FIG. 4E illustrates the detection of ethanol vapors, water, and acetone by the electrochemical sensor of FIG. 4A.

To confirm selectivity of detection, electrochemical sensor 180 was further exposed to water and acetone vapors. Water and acetone are common interferents in various vapor sensing environments. As seen in FIG. 4E, electrochemical sensor 180 has improved detection of ethanol as compared to the detection of water and acetone. The y-axis 250 of FIG. 4E depicts a change in current (I) in nanoamperes (nA). The x-axis 252 of FIG. 4E depicts time in seconds (s). The current (I) for ethanol is about 550 nA and less than 50 nA for water and acetone. Thus, electrochemical sensor 180 has improved detection of ethanol by a ratio of more than ten to one as compared to the detection of water and acetone.

Figure 4F:
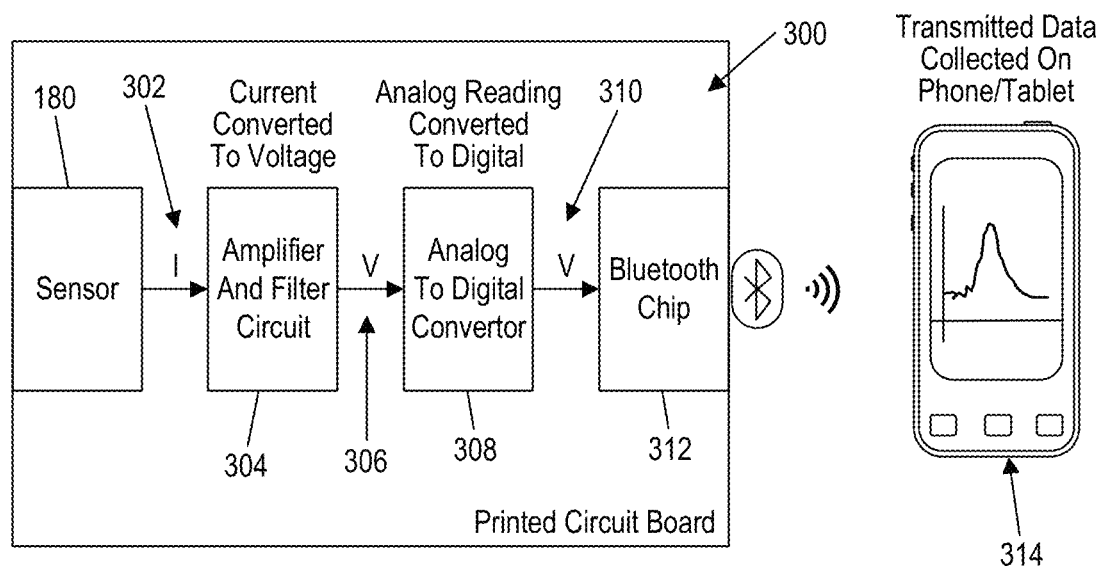
FIG. 4F illustrates the electrochemical sensor of FIG. 4A interfaced with a printed circuit board incorporating Bluetooth technologies.
Figure 4G:
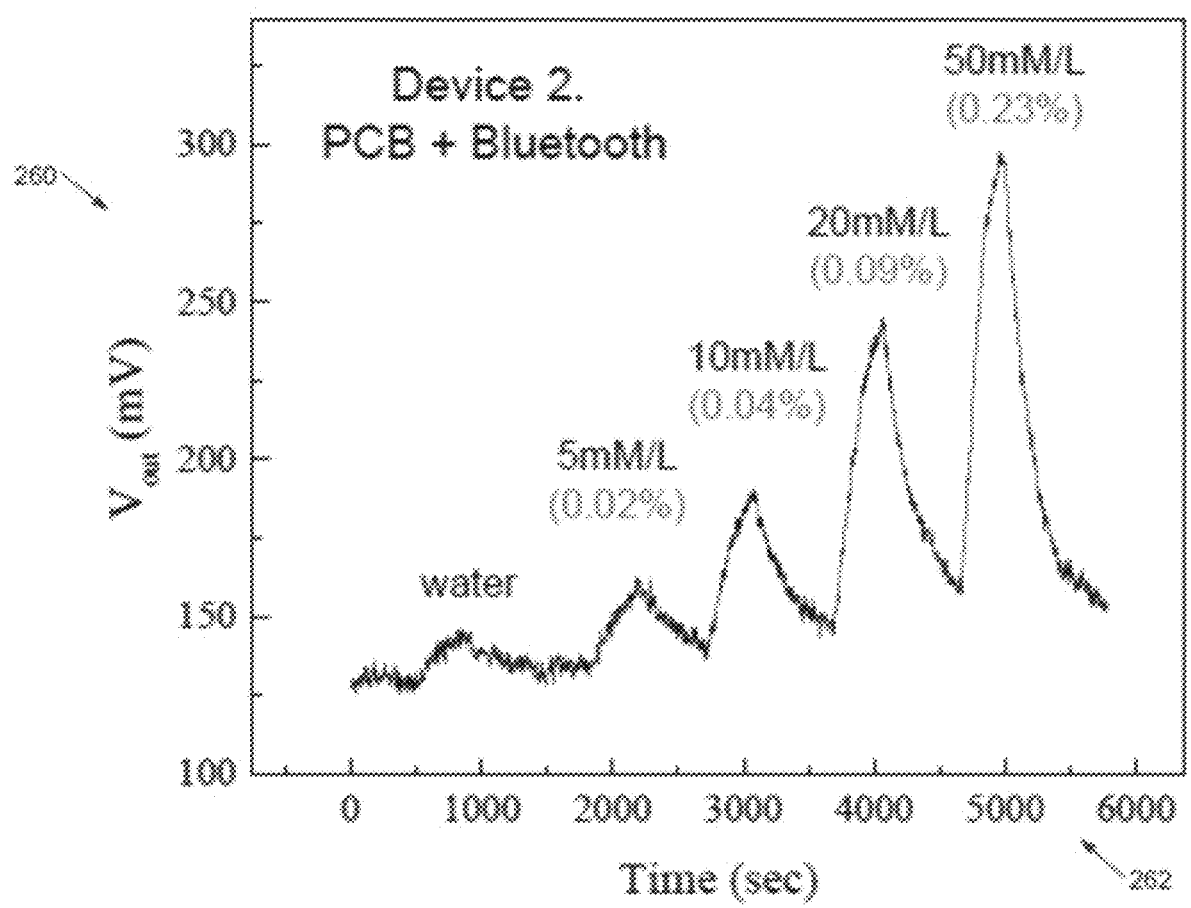
FIG. 4G illustrates the detection of ethanol vapors by the electrochemical sensor and printed circuit board of FIG. 4F.

Electrochemical sensor 180 is compatible with silicon technology and circuity. For example, in certain instances, as seen in FIG. 4F, the electrochemical sensor 180 may be packaged onto a printed circuit board 300. The printed circuit board 300 may amplify and filter the sensor response. Further, the printed circuit board 300 may transmit the results wirelessly to an external computing device 314 (e.g., phone or tablet) using Bluetooth technologies. The printed circuit board 300 seen in FIG. 4F has integrated circuit chips 302 to amplify and filter the detected electronic current (I) 302 and to convert the amplified and filtered electronic current into a voltage (V) reading 306. The analog voltage 306 is converted to a digital voltage 310 using an ADC integrated chip 308 and subsequently transmitted through Bluetooth integrated chip 312 module to an external terminal 314 (e.g., tablet). The electrochemical sensor 180 itself consumes about 100 nWs of power. FIG. 4G illustrates the detection of ethanol concentrations after exposure to vapors from ethanol in water for 100 seconds by an electrochemical sensor 180 interfaces with a printed circuit board 300 having electronic circuity which replaces the voltmeter 202, as seen in FIG. 4F. The y-axis 260 of FIG. 4G depicts voltage out ($V_{out}$) in millivolts (mV). The x-axis 262 of FIG. 4G depicts time in seconds (s). In various embodiments, using the electronic circuity of the printed circuit board 300, a battery having 3.3V (not shown) may be used to generate a DC input (about 1V) or time varying ac input.

EXAMPLE 2

Figure 5A:
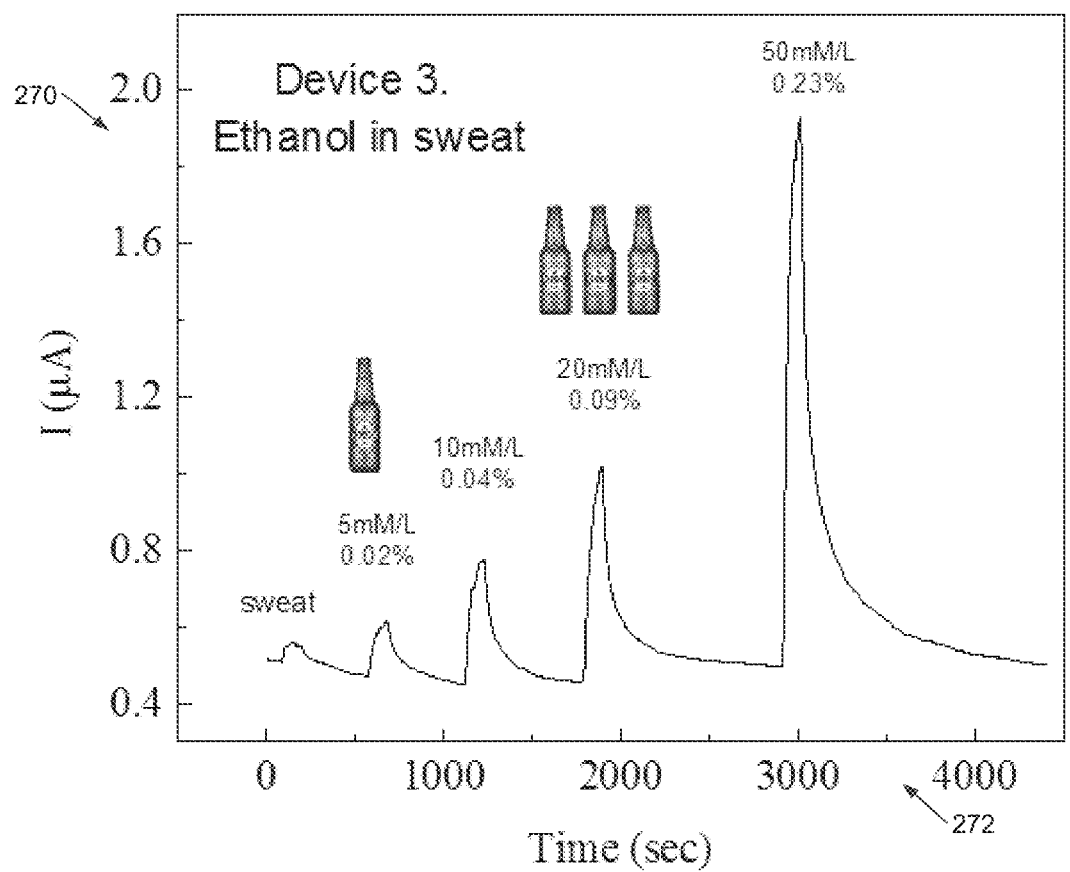
FIG. 5A illustrates the detection of ethanol vapors by an electrochemical sensor prepared in accordance with certain aspects of the present disclosure.
Figure 5B:
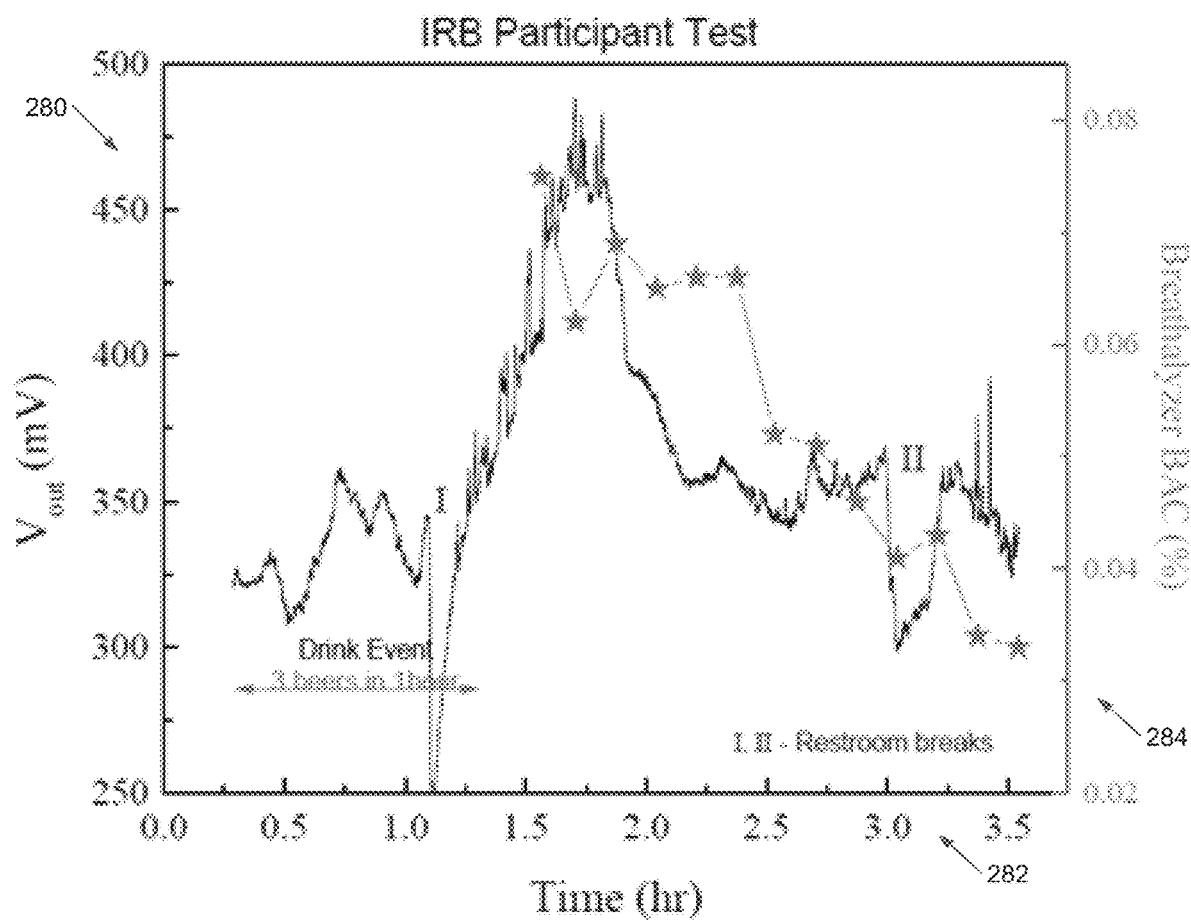
FIG. 5B illustrates the detection of ethanol vapors by the electrochemical sensor of FIG. 5A and the detection of ethanol vapors using conventional breathalyzer methods.
Figure 5C:
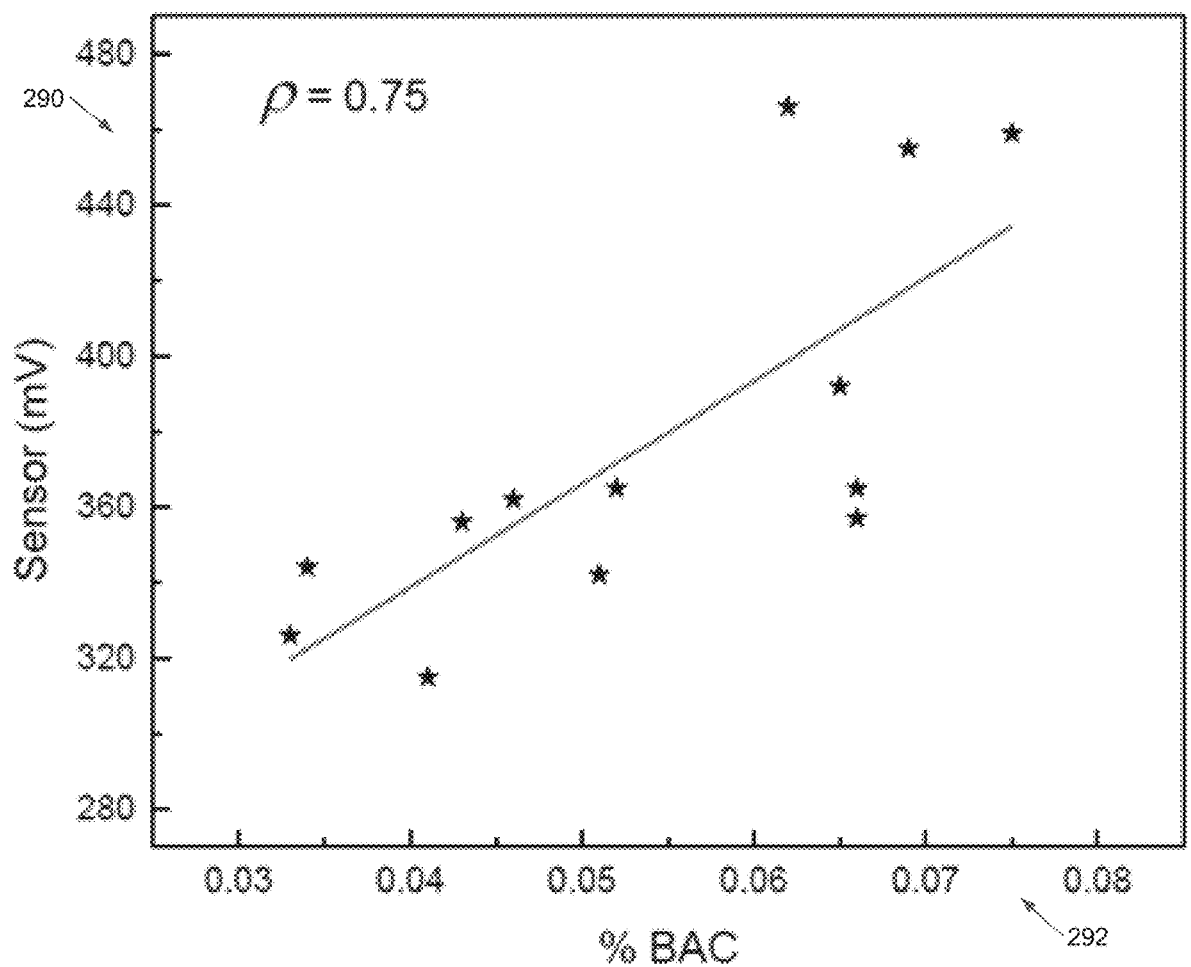
FIG. 5C compares the responses of the electrochemical sensor of FIG. 5A with the responses of a conventional breathalyzer.

Electrochemical sensors in accordance with certain aspects of the present disclosure are useful for practical standalone operations because of their small package, solid-state structure (e.g., no liquid component), and rapid response and high sensitivity to changes within the immediate environment. Further, as noted, the electrochemical sensors of the present disclosure are compatible with conventional electronic technology. The electrochemical sensors presently described can be used to detect clinically relevant chemical markers as well as other point-of-need applications in healthcare, environmental monitoring, and workplace safety. For example only, FIGS. 5A-5C illustrate the use of an electrochemical sensor prepared in accordance with certain aspects of the present disclosure to detect ethanol vapors transpiring through the skin. The detected ethanol vapors may be used in to determine the underlying blood alcohol concentration (BAC). The electrochemical sensor includes a proton exchange membrane including Nafion and a graphene barrier layer similar to electrochemical sensor 180 shown in FIG. 4A.

First, the prepared electrochemical sensor was exposed to vapors from ethanol in sweat for about 100 seconds (s). As seen in FIG. 5A, the prepared electrochemical sensor can detect from as low as about 5 mM ethanol in sweat corresponding to about 0.22 g/dL ethanol or 0.018% BAC (blood concentration ($C_{blood}$)=0.81×sweat concentration ($C_{sweat}$)), which generally corresponds with a 12 ounce bottle of beer (about 5% alcohol) for a 150-pound individual (e.g., the Widmark Formula). Further, as seen in FIG. 5A, the electrochemical sensor responds quickly to alcohol in sweat (e.g., $t_{0\text{-}90\%}^{5mM}=40$ s; $t_{0\text{-}90\%}^{10mM}=72$ s; $t_{0\text{-}90\%}^{50mM}=77$ s; $t_{0\text{-}90\%}^{50mM}=64$ s). The y-axis 270 of FIG. 5A depicts current (I) in microamperes (μA). The x-axis 272 of FIG. 5A depicts time in seconds (s).

Second, the prepared electrochemical sensor was tested using human subjects. Electrochemical sensors were secured to the participants' anterior forearm adjacent to the wrist. The participants subsequently consumed three beers in a one hour span. The twenty participants' wore the electrochemical sensor devices throughout the test. As a benchmark, a police-grade breathalyzer (approximate costs of $250) was used to take readings every twenty minutes after the first hour of drinking. As seen in FIG. 5B, the electrochemical sensor records the underlying blood alcohol concentration (BAC) continuously and with higher resolution than a conventional commercial breathalyzer, which is a single point-in-time measurement. The first or left y-axis 280 of FIG. 5B depicts voltage out ($V_{out}$) in millivolts (mV). The second or right y-axis 282 of FIG. 5B depicts percent Breathalyzer BAC. The x-axis 284 of FIG. 5B depicts time in hours (hr).

Further, skin humidity readings in proximity to the sensor were taken every ten minutes using a Sensirion SHT31 humidity sensor. This data was used to plot the humidity corrected response against the percent Breathalyzer BAC as seen in FIG. 5C, which shows a detected minimum of 0.033% BAC with a Pearson's correlation coefficient (ρ) of 0.75. The average Pearson's correlation coefficient (ρ) for the twenty participants was 0.68. The y-axis 290 of FIG. 5C depicts the sensor readings in millivolts (mV). The x-axis 292 of FIG. 5C depicts percent Breathalyzer BAC (% BAC).

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An electrochemical sensor for detection of analytes, the sensor comprising:
    an ion exchange membrane having a first substantially planar surface opposing a second substantially planar surface;
    a sensing layer having a substantially planar first surface that is substantially parallel with the first surface of the ion exchange membrane, wherein the sensing layer is configured to generate ions in response to one or more select analytes; and
    a first barrier layer sandwiched between the sensing layer and the ion exchange membrane, wherein the first barrier layer includes one or more two-dimensional (2-D) materials selected from the group consisting of: graphene, transition metal dichalcogenides (TMDCs), phosphorene, silicene, germanene, stanene, borophene, and combinations thereof.

2. The electrochemical sensor of claim 1, wherein the ion exchange membrane is further defined as a proton exchange membrane having one or more of $SO_3^-$, $PO_4^-$, and $CO_3^-$ as the proton ion exchange group.

3. The electrochemical sensor of claim 1, wherein the ion exchange membrane is further defined as an anion exchange membrane having quaternary ammonium ($NR_4^+$)/phosphonium ($PR_4^+$) or ammonium polysulfone groups as the anion exchange groups.

4. The electrochemical sensor of claim 1, wherein the sensing layer has a thickness of less than or equal to about 10 nm.

5. The electrochemical sensor of claim 1, wherein the sensing layer includes one or more materials selected from the group consisting of: platinum (Pt), tin (Sn), zinc (Zn), ruthenium (Ru), copper (Cu), titanium (Ti), chromium (Cr), gold (Au), silver (Ag), nickel (Ni), and combinations thereof.

6. The electrochemical sensor of claim 1, wherein the first barrier layer has a thickness of less than or equal to about 1 nm.

7. The electrochemical sensor of claim 1, further comprising:
    a functional layer having a substantially planar first surface that is substantially parallel with the second surface of the ion exchange membrane; and
    a second barrier layer sandwiched between the functional layer and the ion exchange membrane, wherein the second barrier layer comprises a nanomaterial,
    wherein the functional layer and second barrier layer are each configured to complete the ion generating reaction initiated within the sensing layer.

8. The electrochemical sensor of claim 7, further comprising:
    a detection module electrically coupled to at least one of the first barrier layer and the sensing layer and at least one of the second barrier layer and functional layer, wherein the detection module is configured to detect flow of charge between the at least one of the first barrier layer and the sensing layer and the at least one of the second barrier layer and functional layer.

9. The electrochemical sensor of claim 8, wherein the detection module is configured to measure a change in current or voltage traveling therethrough, and the measured change corresponds with an analyte concentration.

10. The electrochemical sensor of claim 8, wherein the detection module is configured to receive a time-varying input from a battery coupled to an electronic circuit, wherein the detection module measures an output change in one of an ac current, ac voltage, capacitance, heterodyne, or combination thereof and correlates the output change with an analyte concentration.

11. The electrochemical sensor of claim 7, wherein the functional layer has a thickness of less than or equal to about 10 nm.

12. The electrochemical sensor of claim 7, wherein the functional layer includes one or more materials selected from the group consisting of: platinum (Pt), tin (Sn), zinc (Zn), ruthenium (Ru), copper (Cu), titanium (Ti), chromium (Cr), gold (Au), silver (Ag), nickel (Ni), and combinations thereof.

13. The electrochemical sensor of claim 7, wherein the second barrier layer has a thickness of less than or equal to about 1 nm.

14. The electrochemical sensor of claim 7, wherein the second barrier layer includes one or more two-dimensional (2-D) materials selected from the group consisting of: graphene, transition metal dichalcogenides (TMDCs), phosphorene, silicene, germanene, stanene, borophene, and combinations thereof.

15. The electrochemical sensor of claim 1, wherein the first barrier layer is a mesh network of one-dimensional (1-D) nanomaterials.

16. The electrochemical sensor of claim 1, wherein the first surface of the ion exchange membrane includes a first portion opposing a second portion and a third portion sandwiched therebetween, wherein a first electrode is disposed on the first portion and a second electrode is disposed on the second portion.

17. The electrochemical sensor of claim 16, wherein the sensing layer is substantially parallel with the third portion of the first surface of the ion exchange membrane.

18. The electrochemical sensor of claim 16, further comprising:
    a detection module electrically coupled to the first electrode and the second electrode, wherein the detection module is configured to detect flow of charge between the first electrode and the second electrode.

19. The electrochemical sensor of claim 18, wherein the detection module is configured to measure a change in current or voltage traveling therethrough, and the measured change corresponds with an analyte concentration.

20. The electrochemical sensor of claim 18, wherein the detection module is configured to receive a time-varying input from a battery coupled to an electronic circuit, wherein the detection module measures an output change in one of an ac current, ac voltage, capacitance, heterodyne, or combination thereof and correlates the output change with an analyte concentration.

21. The electrochemical sensor of claim 16, further comprising:
a separator layer having a first substantially planar surface opposing a second substantially planar surface, the first surface of the separator layer being substantially parallel with the second surface of the ion exchange membrane, wherein the separator is configured to collect generated ions.

22. The electrochemical sensor of claim 21, wherein the separator layer comprises a cellulose based polymer selected from cellulose acetate, ethylene vinyl alcohol, polyamide based polymers, or combinations thereof.

23. The electrochemical sensor of claim 21, further comprising:
a substrate layer having a substantially planar first surface that is substantially parallel with the second surface of the separator layer.

24. An electrochemical sensor for detection of analytes, the sensor comprising:
an ion exchange membrane having a first substantially planar surface opposing a second substantially planar surface;
a first barrier layer disposed on the first surface of the ion exchange membrane, wherein the first barrier layer comprises a two-dimensional (2-D) nanomaterial;
a sensing layer disposed on an exposed substantially planar surface of the first barrier layer opposing the first surface of the ion exchange membrane, wherein the sensing layer is configured to generate ions in response to select analytes;
a second barrier layer disposed on the second surface of the ion exchange membrane, wherein the second barrier layer comprises a two-dimensional (2-D) nanomaterial; and
a functional layer disposed on an exposed substantially planar surface of the second barrier layer opposing the second surface of the ion exchange membrane, wherein the functional layer and second barrier layer are each configured to complete the ion generating reaction initiated within the sensing layer.

25. The electrochemical sensor of claim 24, wherein the ion exchange membrane is further defined as a proton exchange membrane having one or more of $SO_3^-$, $PO_4^-$, and $CO_3^-$ as the proton ion exchange group.

26. The electrochemical sensor of claim 24, wherein the ion exchange membrane is further defined as an anion exchange membrane having quaternary ammonium ($NR_4^+$)/phosphonium ($PR_4^+$) or ammonium polysulfone groups as the anion exchange groups.

27. The electrochemical sensor of claim 24, wherein the sensing layer includes one or more materials selected from the group consisting of: platinum (Pt), tin (Sn), zinc (Zn), ruthenium (Ru), copper (Cu), titanium (Ti), chromium (Cr), gold (Au), silver (Ag), nickel (Ni), and combinations thereof.

28. The electrochemical sensor of claim 24, further comprising:
a detection module electrically coupled to at least one of the first barrier layer and the sensing layer and at least one of the second barrier layer and functional layer, wherein the detection module is configured to detect flow of charge between the at least one of the first barrier layer and the sensing layer and the at least one of the second barrier layer and functional layer.

29. The electrochemical sensor of claim 28, wherein the detection module is configured to measure a change in current or voltage traveling therethrough, and the measured change corresponds with an analyte concentration.

30. An electrochemical sensor for detection of analytes, the sensor comprising:
an ion exchange membrane having a first substantially planar surface opposing a second substantially planar surface, the first surface having a first portion distal from a second portion and a third portion sandwiched therebetween;
a barrier layer disposed on the third portion of the first surface of the ion exchange membrane, wherein the barrier layer comprises a two-dimensional (2-D) nanomaterial;
a sensing layer disposed on an exposed substantially planar surface of the barrier layer opposing the third portion of the first surface of the ion exchange membrane, wherein the sensing layer is configured to generate ions in response to select analytes;
a first electrode disposed on the first portion of the first surface of the ion exchange membrane;
a second electrode disposed on the second portion of the first surface of the ion exchange membrane;
a separator layer disposed on the second surface of the ion exchange membrane, wherein the separator is configured to collect the generated ions; and
a substrate layer disposed on an exposed substantially planar surface of the separator opposing the second surface of the ion exchange membrane.

31. The electrochemical sensor of claim 30, wherein the ion exchange membrane is further defined as a proton exchange membrane having one or more of $SO_3^-$, $PO_4^-$, and $CO_3^-$ as the proton ion exchange group.

32. The electrochemical sensor of claim 30, wherein the ion exchange membrane is further defined as an anion exchange membrane having quaternary ammonium ($NR_4^+$)/phosphonium ($PR_4^+$) or ammonium polysulfone groups as the anion exchange groups.

33. The electrochemical sensor of claim 30, wherein the sensing layer includes one or more materials selected from the group consisting of: platinum (Pt), tin (Sn), zinc (Zn), ruthenium (Ru), copper (Cu), titanium (Ti), chromium (Cr), gold (Au), silver (Ag), nickel (Ni), and combinations thereof.

34. The electrochemical sensor of claim 30, further comprising:
a detection module electrically coupled to at least one of the first barrier layer and the sensing layer and at least one of the second barrier layer and functional layer, wherein the detection module is configured to detect flow of charge between the at least one of the first barrier layer and the sensing layer and the at least one of the second barrier layer and functional layer.

35. The electrochemical sensor of claim 34, wherein the detection module is configured to measure a change in current or voltage traveling therethrough, and the measured change corresponds with an analyte concentration.

36. An electrochemical sensor for detection of analytes, comprising:
- an ion exchange membrane having a first substantially planar surface opposing a second substantially planar surface;
- a first barrier layer disposed on the first surface of the ion exchange membrane, wherein the first barrier layer is a mesh network of one-dimensional nanomaterial;
- a sensing layer disposed on an exposed substantially planar surface of the first barrier layer opposing the first surface of the ion exchange membrane, wherein the sensing layer is configured to generate ions in response to select analytes;
- a second barrier layer disposed on the second surface of the ion exchange membrane, wherein the second barrier layer comprises a two-dimensional (2-D) nanomaterial; and
- a functional layer disposed on an exposed substantially planar surface of the second barrier layer opposing the second surface of the ion exchange membrane, wherein the functional layer and second barrier layer are each configured to complete the ion generating reaction initiated within the sensing layer.

37. The electrochemical sensor of claim 36, wherein the ion exchange membrane is further defined as a proton exchange membrane having one or more of $SO_3^-$, $PO_4^-$, and $CO_3^-$ as the proton ion exchange group.

38. The electrochemical sensor of claim 36, wherein the ion exchange membrane is further defined as an anion exchange membrane having quaternary ammonium ($NR_4^+$)/phosphonium ($PR_4^+$) or ammonium polysulfone groups as the anion exchange groups.

39. The electrochemical sensor of claim 36, wherein the sensing layer includes one or more materials selected from the group consisting of: platinum (Pt), tin (Sn), zinc (Zn), ruthenium (Ru), copper (Cu), titanium (Ti), chromium (Cr), gold (Au), silver (Ag), nickel (Ni), and combinations thereof.

40. The electrochemical sensor of claim 36, further comprising:
- a detection module electrically coupled to at least one of the first barrier layer and the sensing layer and at least one of the second barrier layer and functional layer, wherein the detection module is configured to detect flow of charge between the at least one of the first barrier layer and the sensing layer and the at least one of the second barrier layer and functional layer.

41. The electrochemical sensor of claim 36, wherein the detection module is configured to measure a change in current or voltage traveling therethrough, and the measured change corresponds with an analyte concentration.

* * * * *